United States Patent [19]

Haber et al.

[11] Patent Number: 5,681,574
[45] Date of Patent: Oct. 28, 1997

[54] PAD APPLICATOR FOR A REHYDRATED MULTI-CONSTITUENT MEDICATION

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 302,587

[22] Filed: Sep. 8, 1994

[51] Int. Cl.$^6$ ................................................ A01N 25/34
[52] U.S. Cl. ................................ 424/402; 424/401
[58] Field of Search .......................... 424/401, 402; 401/132, 196; 514/844, 846, 848, 859

[56] References Cited

U.S. PATENT DOCUMENTS

| | | | |
|---|---|---|---|
| 4,140,409 | 2/1979 | DeVries | 401/132 |
| 4,533,540 | 8/1985 | Blank | 424/28 |
| 4,812,067 | 3/1989 | Brown et al. | 401/132 |
| 5,254,109 | 10/1993 | Smith et al. | 604/289 |
| 5,326,564 | 7/1994 | LaRosa et al. | 424/401 |

Primary Examiner—Thurman K. Page
Assistant Examiner—Sharon Howard
Attorney, Agent, or Firm—Morland C. Fischer

[57] ABSTRACT

A compact, single use pad applicator is disclosed having a dry medication (e.g. a dehydrated topical astringent disinfectant that is adapted to treat acne and has been reduced to crystalline form by lyophilization) stored in a first chamber. A liquid diluent is stored in a second chamber. Fluid communication between the first and second chambers is blocked by a normally closed, pressure activated valve or seal. By compressing the second chamber, a corresponding hydraulic pressure is generated in the diluent which opens the valve. Accordingly, the diluent in the second chamber is introduced under pressure to the dry medication in the first chamber to rehydrate and activate the acne medication. The reconstituted multi-constituent liquid medication is absorbed by a pad-shaped swab so as to be applied directly to a relatively wide tissue area as a topical treatment for acne or other skin disorders.

16 Claims, 5 Drawing Sheets

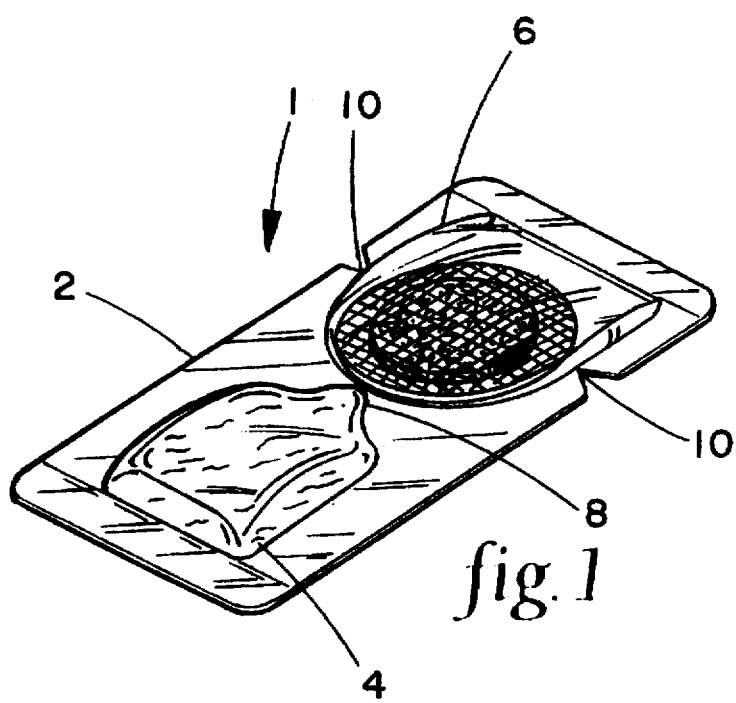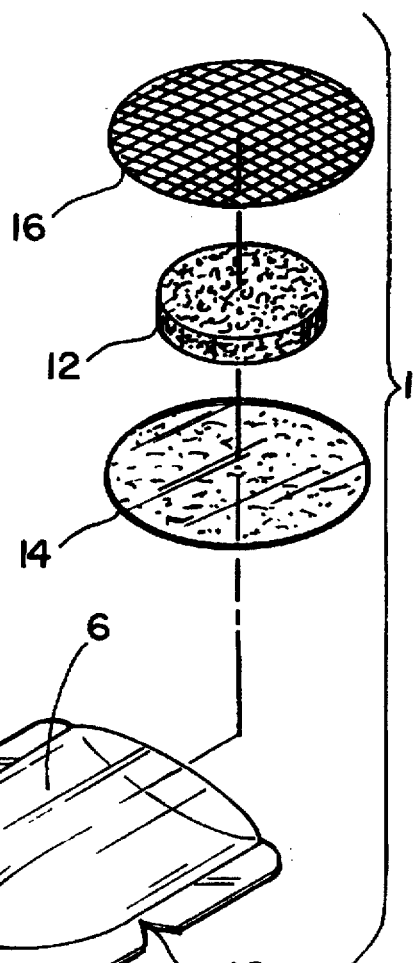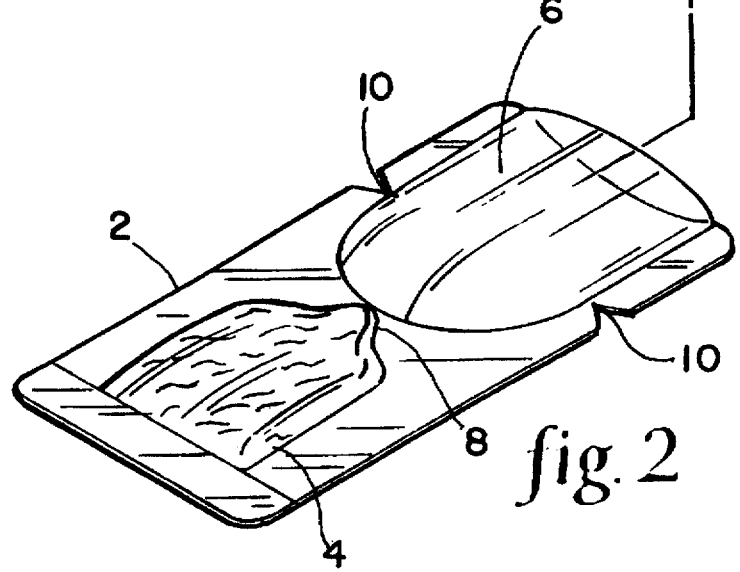

PAD APPLICATOR FOR A REHYDRATED MULTI-CONSTITUENT MEDICATION

BACKGROUND OF THE INVENTION

1. Field of the Invention

This invention relates to a compact, single use pad applicator in which a lyophilized medication is packaged in a wafer or powder form to be rehydrated prior to use by a liquid diluent so that a precise amount of the reconstituted medication can be applied from an absorbent pad directly to a target site for the treatment of acne, and the like.

2. Background Art

It is sometimes desirable for those suffering from acne or other skin disorders to periodically apply a topical medication to a tissue area to enhance treatment and speed healing. It is common to package the topical acne medication as a liquid or cream in a bottle or tube or as a series of moist pads in a jar. Because the liquid, cream and moisture is subject to evaporation with time, the shelf life of the usual packaged medication may be undesirably shortened. Moreover, once the container is opened and the medication is exposed to the atmosphere, some of the moist treatment pads may dry out while some of the liquid or cream medication may evaporate or be spilled.

In addition, it may not be convenient to carry on one's person a relatively large container in which the liquid medication or moist pads are packaged. More particularly, the user may have to transport a bottle, tube or jar even though only a small portion of the medication therein will be used during any given treatment. In this same regard, there is no readily available way for the user to control the application of a precise amount of acne medication to this tissue. Too much or too little liquid or cream is often dispensed from a bottle or tube. For example, if the tissue area to be treated is small, the moist pad is known to have an excess of medication than that actually needed to adequately treat the acne.

The foregoing results in inefficiency and/or waste which can prove to be inconvenient, particularly if the medication is expensive or the acne requires a long period of treatment. In some cases, the user may have to replace the medication prematurely, because of the evaporation or inefficient use thereof. In other cases, the user may elect to forego treatment altogether, especially when travelling far from home.

SUMMARY OF THE INVENTION

In general terms, a compact, low profile and single use pad applicator is disclosed in which a multi-constituent medication is packaged and ready to be activated for direct application to a target site. According to a first embodiment of the invention, the applicator includes a generally planar body having a bubble-shaped proximal chamber located at one end thereof and a distal chamber located at the opposite end. The body and proximal and distal chambers are each manufactured from a gas and liquid impermeable, heat sealable material. A pair of scored areas are formed in opposite sides of the body to form a lateral tear line thereacross. A normally closed (i.e. sealed) pressure activated valve (i.e. orifice) extends between the proximal and distal chambers. Located within the distal chamber is a medication wafer. The medication wafer is preferably a dehydrated topical astringent disinfectant that is known to treat acne and that has been reduced to crystalline form by a conventional lyophilization process. The medication wafer is sandwiched between a liquid impervious backing and an absorbent disk-like pad. A liquid diluent (e.g. a saline solution) is stored in the proximal chamber and separated from the medication wafer in the distal chamber by the normally closed valve.

To activate and use the pad applicator of the first embodiment, the user first squeezes the bubble-shaped proximal chamber so as to apply compressive forces thereagainst and generate a corresponding hydraulic pressure within the diluent. The hydraulic pressure of the diluent ruptures (i.e. opens) the seal of the normally closed valve so that the former barrier between the proximal and distal chambers is now removed to permit the liquid diluent to be introduced, under pressure, to the medication wafer. Accordingly, the dry astringent disinfectant of the medication wafer is mixed with the diluent and rehydrated to a liquid medication which is absorbed through the absorbent pad by means of capillary action. Next, the user tears the body of the pad applicator along the lateral tear line between the preformed scored areas. When the body is torn, the distal chamber is broken and opened. Accordingly, the disk-like pad which has absorbed the reconstituted liquid medication will now be exposed and accessible to the user. Finally, the user moves the saturated pad into contact with the tissue to be treated so that the reconstituted acne medication can be applied directly to the target site. When the topical treatment has been completed, the spent applicator is simply discarded.

According to a second embodiment of the invention, the applicator includes a generally planar body having a bubble-shaped chamber located at one end thereof and an access opening located through the opposite end. Located below and in axial alignment with the access opening through the body is a medication wafer. The medication wafer is preferably a dehydrated topical astringent disinfectant that is known to treat acne and that has been reduced to crystalline form by a conventional lyophilization process. The medication wafer is sandwiched between a liquid impervious backing and an absorbent disk-like pad. An adhesive-backed base is bonded to the underside of the applicator body to urge the absorbent pad through the access opening in the body. A removable cover is adhesively bonded to the top side of the body so as to surround and protect the absorbent pad projecting through the access opening. A liquid diluent (e.g. a saline solution) is stored in the bubble-shaped chamber and separated from the medication wafer below the removable cover by a normally closed (i.e. sealed) pressure activated valve (i.e. orifice) that extends between the bubble-shaped chamber and the removable cover.

To activate and use the pad applicator of the second embodiment, the user first squeezes the bubble-shaped chamber so as to apply compressive forces thereagainst and generate a corresponding hydraulic pressure within the diluent. The hydraulic pressure of the diluent ruptures (i.e. opens) the seal made by the normally closed valve so that the former barrier between the bubble-shaped chamber and the removable cover is now dissolved to permit the liquid diluent to be introduced, under pressure, to the medication wafer. Accordingly, the dry astringent disinfectant of the medication wafer is mixed with the diluent and rehydrated to a liquid medication which is absorbed through the absorbent pad by means of capillary action. Next, the user tears the removable cover away from the applicator body so as to expose the absorbent pad which projects through the access opening. Accordingly, the disk-like pad which has absorbed the reconstituted liquid medication will now be accessible to the user. Finally, the user moves the saturated pad into contact with the tissue to be treated so that the reconstituted acne medication can be applied directly to the target site. When the topical treatment has been completed, the spent applicator is simply discarded.

BRIEF DESCRIPTION OF THE DRAWINGS

FIG. 1 is a perspective view of a compact, single use pad applicator according to a first embodiment of the present invention in the packaged, ready-to-activate configuration;

FIG. 2 is an exploded view of the pad applicator of FIG. 1;

DETAILED DESCRIPTION

Figure 3:
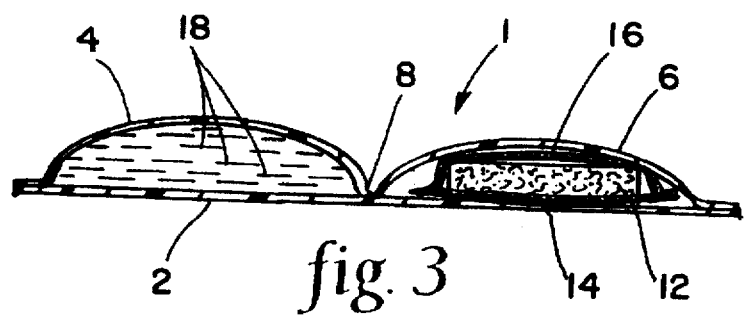
FIG. 3 is a cross-section of the pad applicator of FIG. 1.

FIGS. 1-4B of the drawings illustrate a first embodiment for a compact and low profile, single use pad applicator in which a topical acne medication is packaged for application by a user directly to a target site for the treatment of acne. Referring initially to FIGS. 1-3, an applicator 1 is shown according to a first embodiment of the present invention for dispensing a precise amount of acne medication to a relatively wide tissue area requiring treatment. The applicator 1 includes a generally planar body 2 having a hollow bubble-shaped proximal chamber 4 extending from one end of the body and a hollow distal chamber 6 extending from the opposite end. The body 2 and proximal and distal chambers 4 and 6 of the pad applicator 1 are manufactured from a gas and liquid impermeable, heat sealable material that is suitable for thermal bonding. By way of example, one such material which may be used to manufacture the pad applicator 1 is a commercially available Mylar/polyethylene barrier layer material. To this end, the proximal and distal chambers 4 and 6 are heat sealed against the body 2 to form air and liquid-tight closures at the interface therewith (best shown in FIG. 3).

In the packaged, ready-to-activate applicator assembly 1 best shown in FIG. 1, the proximal and distal chambers 4 and 6 are isolated from one another by a normally closed, pressure actuated valve 8. Valve 8 is a relatively narrow fluid orifice that is integrally formed with and projects outwardly from the proximal chamber 4 to communicate with the distal chamber 6. However, and as is best shown in FIG. 3, the valve 8 is, in the packaged condition of applicator 1, sealed and closed against the body 2. A pair of scored (e.g. notched) areas 10 are formed in the sides of the applicator body 2 in opposing alignment with one another across the distal chamber 6. As will be disclosed in greater detail hereinafter, the scored areas 10 form a lateral tear line through the applicator body 2 to permit the distal chamber 6 to be broken and opened.

Sealed within the distal chamber 6 is a medication wafer 12. The medication wafer 12 is preferably a dehydrated topical astringent disinfectant for treating acne that has been reduced to crystalline form by a conventional lyophilization process. However, the dehydrated disinfectant could also take the form of a powder rather than a wafer. As is best shown in FIG. 3, the medication wafer 12 sits upon a disk-like, liquid impermeable backing 14 and is covered by an absorbent disk-like pad 16. The backing 14 has an adhesive top surface for retaining the medication wafer 12 thereon and for bonding to the absorbent pad 16 thereabove. That is, the medication wafer 12 is sandwiched between backing 14 and pad 16. The absorbent pad 16 is formed from cotton or a suitable open cell foam material.

In the packaged, ready-to-activate applicator assembly 1 shown in FIG. 3, a liquid diluent (e.g. a saline solution) is stored in the bubble-shaped proximal chamber 4. As will soon be disclosed, the diluent 18 of proximal chamber 4 can be introduced to and mixed with the dehydrated disinfectant of medication wafer 12 in the distal chamber 6 by way of valve 8 to rehydrate and activate the medication when the user is ready to treat his acne.

Figure 4A:
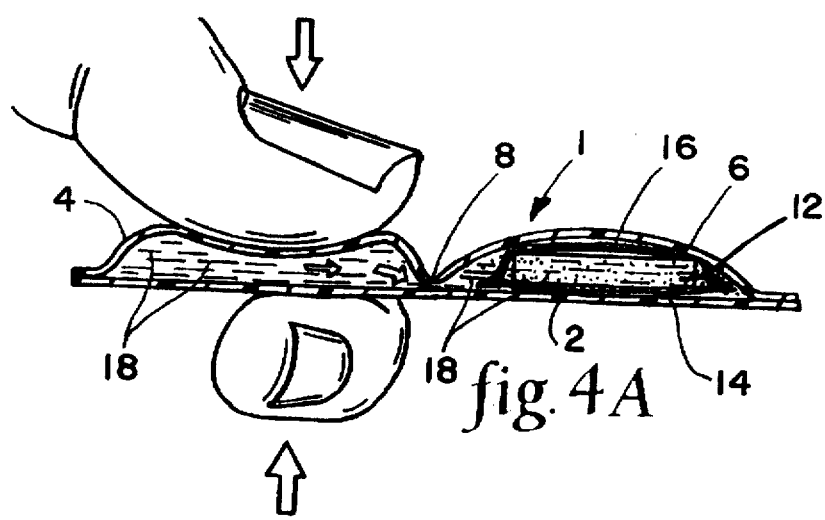
FIGS. 4A and 4B are illustrative of the steps by which to activate and use the pad applicator of FIG. 1.

The activation and use of the pad applicator 1 to apply a topical acne medication to a target site is initially disclosed while referring to FIG. 4A. First, the user squeezes the bubble-shaped proximal chamber 4 (e.g. between his thumb and forefinger, as illustrated) so as to apply opposing compressive forces thereagainst in the direction of the reference arrows. The compressive forces applied to the proximal chamber 4 create a corresponding hydraulic pressure within the diluent 18. The user continues to compress the proximal chamber 4 until the hydraulic pressure is sufficient to rupture (i.e. open) the seal established by the normally closed valve 8 against the body 2. The valve 8 is forced away from the body 2 so that the former barrier between the diluent 18 and the medication wafer 12 is removed and the proximal and distal chambers 4 and 6 are placed in fluid communication with one another, whereby to permit the liquid diluent 18 to be introduced, under pressure, to the medication wafer 12.

Accordingly, the dry astringent disinfectant of wafer 12 is now mixed with the diluent and rehydrated to a liquid medication 20 (best shown in FIG. 4B) which is absorbed through the absorbent pad 16 by means of capillary action. In this regard, it may be appreciated that the liquid impermeable backing 14 on which the medication wafer 12 is seated urges and directs the flow of the liquid diluent 18 towards the pad 16 so that the reconstituted medication 20 may be better absorbed thereby. It may be further appreciated that the pad 16 is located within a sealed environment provided by the distal chamber 6 so as to prevent the loss of the liquid diluent 18 and improve the efficiency by which the diluent is absorbed by the pad 16.

Figure 4B:
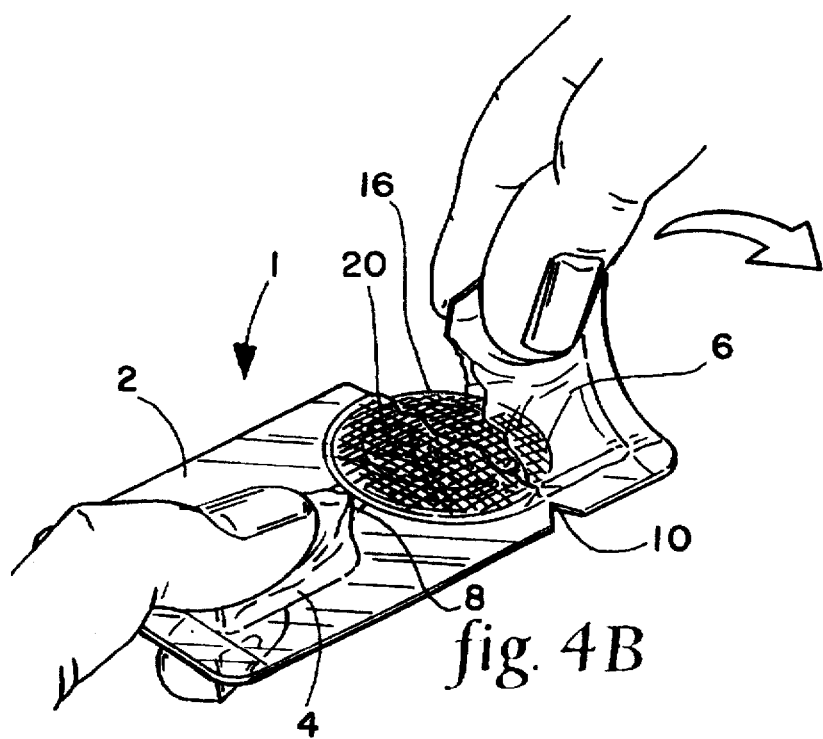

Next, and referring now to FIG. 4B, while squeezing and compressing the proximal chamber 4 of pad applicator 1 with one hand, the user grasps the body 2 with the other hand and applies a pulling force thereto so as to tear the body 2 of applicator 1 along a lateral tear line between the preformed scored areas 10. When the body 2 is torn, as illustrated, the sealed environment provided by the distal chamber 6 will be broken and opened. Accordingly, the disk-like pad 16 which has absorbed the reconstituted liquid medication 20 is exposed and accessible to the user. Finally, the user moves the saturated pad 16 into contact with the tissue to be treated so that the acne medication 20 can be applied directly to and swabbed over a relatively wide target site. When the topical treatment has been completed, the spent applicator is simply discarded.

Figure 5:
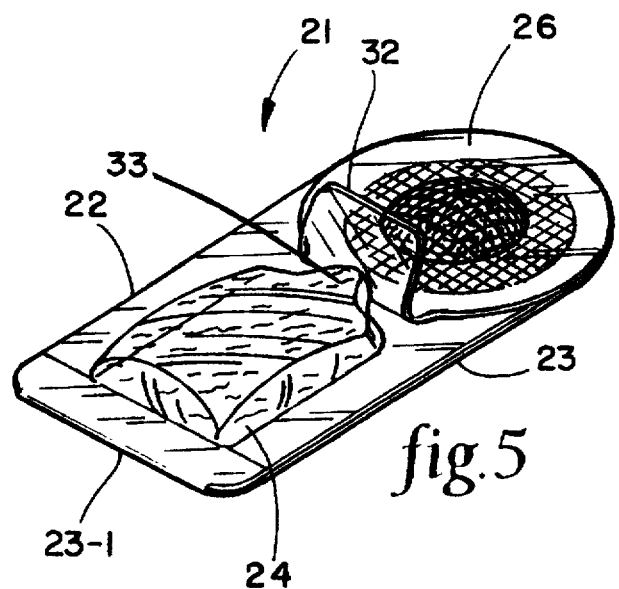
FIG. 5 is a perspective view of a compact, single use pad applicator according to a second embodiment of the invention in the packaged, ready-to-activate configuration.
Figure 6:
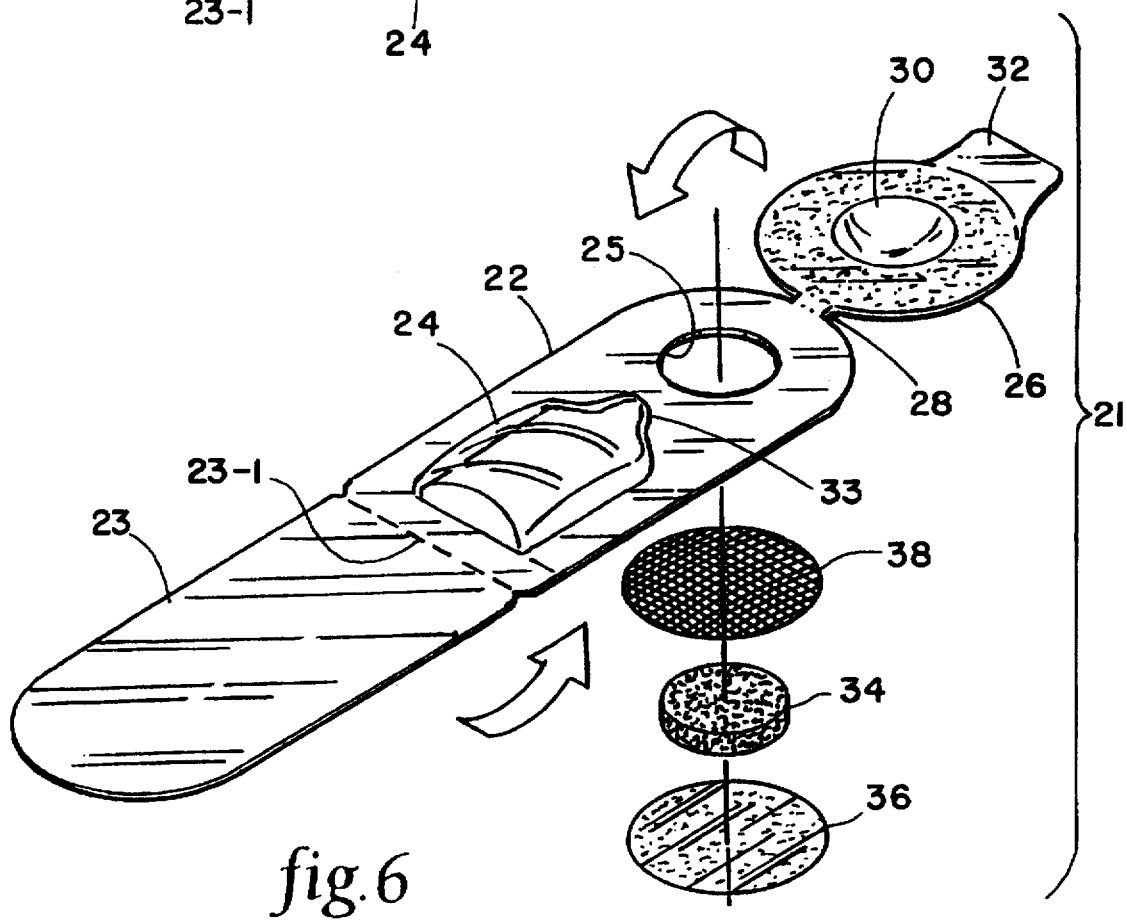
FIG. 6 is an exploded view of the pad applicator of FIG. 5.
Figure 7:
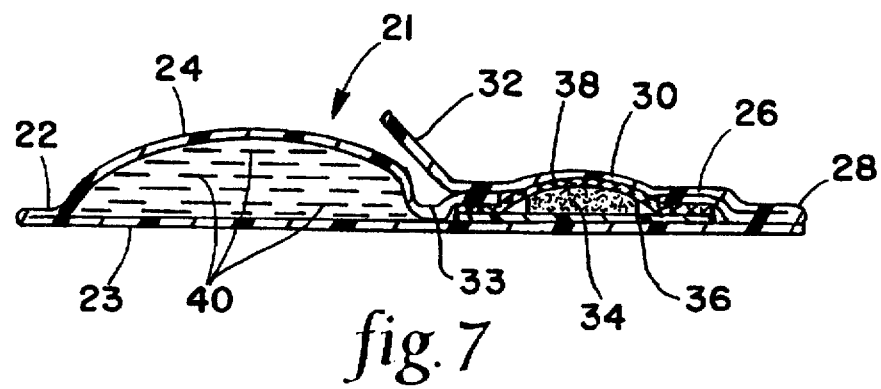
FIG. 7 is a cross-section of the pad applicator of FIG. 5.

FIGS. 5-9 of the drawings illustrate a second embodiment for a compact, low profile and single use pad applicator in which a topical acne medication is packaged to be applied directly from an absorbent pad to a tissue area in need of treatment. Referring initially to FIGS. 5, 6 and 7, another applicator 21 is shown for applying a precise amount of medication to a relatively wide target area. Applicator 21 includes a generally planar body 22 and a generally planar base 23. The body 22 and the base 23 of applicator 21 are joined together and rotatable relative to one another along a fold line 23-1 (of FIG. 6). The underside of the base 23 is covered with an adhesive (not shown) so that, as will be disclosed in greater detail hereinafter, the base can be rotated downwardly around fold line 23-1 and adhesively bonded to the underside of base 22.

A bubble-shaped chamber 24 is located at one side of the body 22 of applicator 21 and an access hole 25 is formed through the opposite end. The body 22, base 23 and chamber 24 are all manufactured from a gas and liquid impermeable, heat sealable (e.g. a Mylar/polyethylene) material that is suitable for thermal bonding. A removable cover 26 is joined to the body 22 (at the end thereof opposite the end which is joined to base 23) by a narrow, flexible joint 28. A hemispherical cap 30 projects upwardly from the cover 26, and a pull tab 32 projects outwardly therefrom. The top side of cover 26 is covered by an adhesive so that, as will also be disclosed, the cover 26 can be rotated at flexible joint 28 and adhesively bonded to the top side of the base 22.

The pad applicator 21 also includes a medication wafer (or powder) 34. Medication wafer 34 is preferably a dehydrated topical astringent disinfectant for treating acne that has been reduced to crystalline form by lyopilization. As is best shown in the packaged, ready-to-activate applicator assembly 1 of FIG. 7, the medication wafer 34 sits on a disk-like liquid impermeable backing 36 and is covered by an absorbent (e.g. cotton or an open cell foam material) disk-like pad 38. The backing 36 has an adhesive top surface for retaining the medication wafer 34 thereon and for bonding to the absorbent pad 38 thereabove. That is, the medication wafer 34 is sandwiched between backing 36 and pad 38.

To complete the packaged, ready-to-activate assembly of FIG. 3, the sandwich comprising the medication wafer 34 between backing 36 and absorbent pad 38 is positioned at the underside of the body 22 of applicator 21 so that the pad 38 is in axial alignment with the access hole 25 through body 22. The base 23 is then rotated around fold line 23-1 so as to be moved towards and adhesively bonded against the underside of the body 22 to urge the absorbent pad 38 to extend through the access hole 25 in body 22. Alternatively, the base 23 may be thermally bonded to the underside of the body 22. Next, the removable cover 26 is rotated at flexible joint 28 so as to be moved towards and adhesively bonded against the top side of the body 22 with the hemispherical cap 30 of cover 26 surrounding and protecting the absorbent pad 38 extending through access hole 25 and the pull tab 32 of cover 26 positioned in easy reach of the user.

As is also best shown in FIG. 3, a liquid diluent 40 (e.g. a saline solution) is stored in the bubble-shaped chamber 24. As will soon be disclosed, the diluent 40 in chamber 24 can be introduced to and mixed with the dehydrated disinfectant of medication wafer 32 by way of a normally closed, pressure activated valve 33. Valve 33 is a relatively narrow fluid orifice that is integrally formed with and projects outwardly from the bubble-shaped chamber 24 and is adapted to open a fluid path between chamber 24 and the medication wafer 34 located below the cover 26. However, in the packaged applicator assembly 1, the valve 33 is sealed and closed against the body 22 to establish a barrier between the diluent 40 of chamber 24 and the medication wafer 34 located below removable cover 26 and protected by the below hemispherical cap 30 thereof.

The activation and use of the pad applicator 21 according to this second embodiment to apply a topical acne medication to a target site is initially disclosed while referring to FIG. 8. First, the user squeezes the bubble-shaped chamber 24 (e.g. between his thumb and forefinger, as illustrated) so as to apply opposing compressive forces thereagainst in the direction of the reference arrows. The compressive forces applied to the chamber 24 create a corresponding hydraulic pressure within the diluent 40. The user continues to compress the proximal chamber 24 until the hydraulic pressure is sufficient to rupture (i.e. open) the seal established by the normally closed valve 33 against the body 22. The valve 33 is forced away from the body 22 so that the former barrier between the diluent 40 and the medication wafer 34 is removed and the chamber 24 and the cover 26 are placed in fluid communication with one another, whereby to permit the liquid diluent 40 to be introduced, under pressure, to the medication wafer 34.

Accordingly, the dry astringent disinfectant of wafer 34 is now mixed with the diluent and rehydrated to a liquid medication 42 which is absorbed through the absorbent pad 38 by means of capillary action. In this regard, it may be appreciated that the liquid impermeable backing 36 on which the medication wafer 34 is seated urges and directs the flow of the liquid diluent 40 towards the pad 38 so that the reconstituted medication may be better absorbed thereby. It may be further appreciated that the pad 38 is located within a sealed environment provided by the protective hemispherical cap 30 of removable cover 26 so as to prevent the loss of the liquid diluent 40 and improve the efficiency by which the liquid medication 42 is absorbed by the pad 38.

Figure 8A:
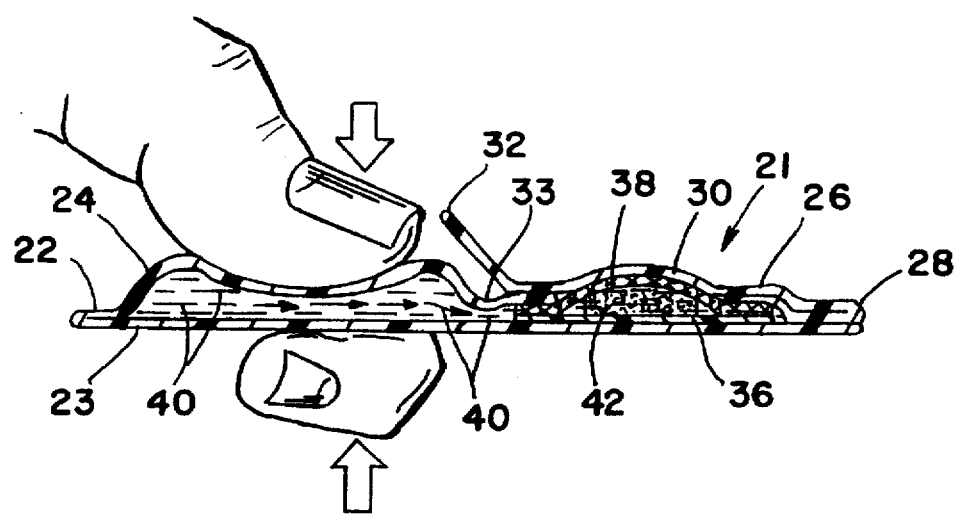
FIGS. 8A, 8B and 9 are illustrative of the steps by which to activate and use the pad applicator of FIG. 5.
Figure 8B:
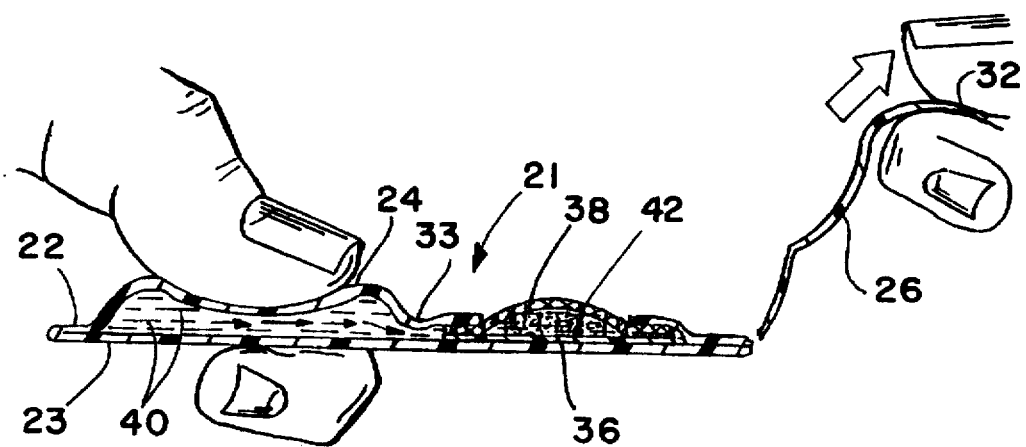

Next, and referring to FIG. 8B, while squeezing and compressing the bubble-shaped chamber 24 of pad applicator 21 with one hand, the user grasps the pull tab 32 of removable cover 26 with the other hand and applies a pulling force thereto so as to tear off the cover 26 at the narrow flexible joint 28 (of FIG. 8A). When the cover 26 is torn off and removed from the body 22 of applicator 21, as illustrated, the sealed environment previously provided by cover 26 is now opened. Accordingly, the disk-like pad 38 which has absorbed the reconstituted liquid medication 42 is exposed and accessible to the user.

Figure 9:
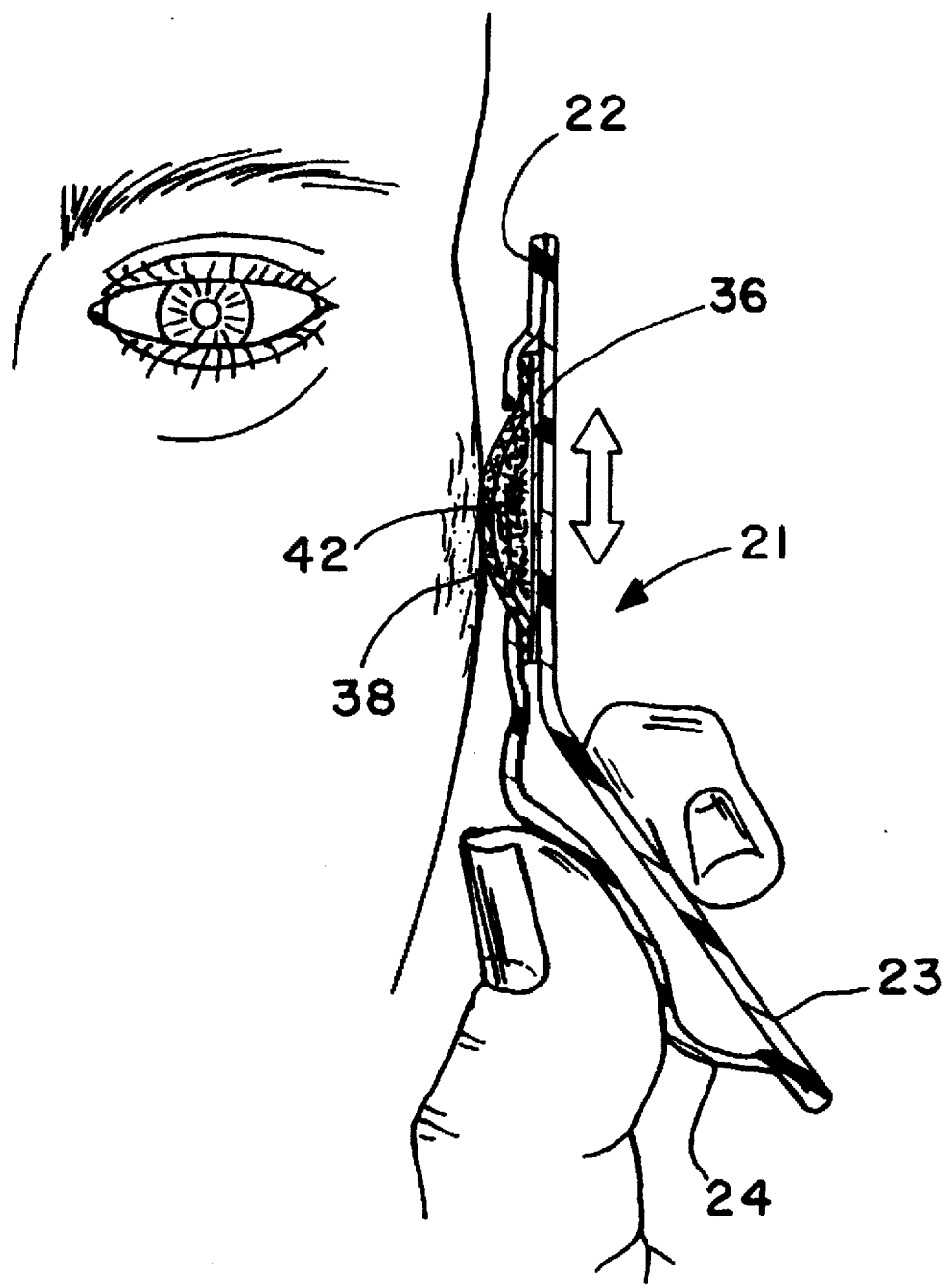

Finally, and as is illustrated in FIG. 9, the user moves the applicator 21 towards his face and places the saturated pad 38 in contact with the tissue to be treated so that the acne medication 42 can be applied directly from pad 38 and swabbed over a relatively wide target site. When the topical treatment has been completed, the spent applicator is simply discarded.

It will be apparent that while the preferred embodiments of the invention have been shown and described, various modifications and changes may be made without departing from the true spirit and scope of the invention. For example, while the reconstituted medication has been disclosed herein as being adapted to treat acne, this should not be considered as a limitation of the invention. In this regard, it is to be understood that the topical astringent disinfectant to be applied to the tissue of the user may be used to treat skin disorders, other than acne.

Having thus set forth the preferred embodiments, what is claimed is:

1. An applicator for applying a liquid medication to a tissue area in need of treatment, said applicator comprising:

a body;

a flexible first chamber closed against said body;

a liquid stored within said first chamber;

a second chamber closed against said body;

a dry medication stored within said second chamber;

absorbent means located in said second chamber and communicating with said dry medication;

a fluid orifice extending between said first and second chambers, said fluid orifice being sealed against said body to close said fluid orifice and thereby block the introduction of the liquid in said first chamber to the dry medication in said second chamber, said flexible first chamber being responsive to a compressive force applied thereto to generate a corresponding hydraulic pressure within said liquid to unseal said fluid orifice from said body to open said fluid orifice and thereby establish a fluid path between said first and second chambers so that said liquid in said first chamber can be introduced to and mixed with said dry medication in said second chamber to produce a liquid medication to be absorbed by said absorbent means; and means by which to open said second chamber to expose said absorbent means therewithin so that said absorbent means can be moved into contact with the tissue area in need of treatment to apply the liquid medication thereto.

2. The applicator recited in claim 1, wherein said dry medication is a dehydrated liquid disinfectant that is rehydrated when said liquid is introduced thereto to produce said liquid medication.

3. The applicator recited in claim 2, wherein said dehydrated liquid disinfectant is a crystalline solid having a wafer shape.

4. The applicator recited in claim 1, further comprising a liquid impermeable backing located within said second chamber, said dry medication positioned between said absorbent means and said liquid impermeable backing to improve the efficiency by which said absorbent means absorbs said liquid medication.

5. The applicator recited in claim 4, wherein said absorbent means is an absorbent pad and said liquid impermeable means is a disk, said liquid impermeable disk having an adhesive surface whereby said disk is adhesively bonded to said absorbent pad with said dry medication sandwiched therebetween.

6. The applicator recited in claim 1, wherein said means by which to open said second chamber includes a lateral tear line extending across said body and through said second chamber, said body being severed along said lateral tear line to rupture said second chamber and expose said absorbent means therewithin.

7. An applicator for applying a liquid medication to a tissue area in need of treatment, said applicator comprising:

a body having a top, a bottom and an access opening extending therethrough;

a flexible chamber closed against the top of said body;

a liquid stored within said flexible chamber;

a removable closure detachably connected to the top of said body to surround said access opening;

absorbent means located at the bottom of said body and projecting upwardly through said access opening to be surrounded by said removable closure at the top of said body;

a dry medication located at the bottom of said body in axial alignment with said access opening so as to communicate with said absorbent means within said removable closure;

a fluid orifice extending between said flexible chamber and said removable closure, said fluid orifice being sealed against the top of said body to close said fluid orifice and thereby block the introduction of the liquid in said flexible chamber to the dry medication below said removable closure, said flexible chamber being responsive to a compressive force applied thereto to generate a corresponding hydraulic pressure within said liquid to unseal said fluid orifice from the top of said body to open said fluid orifice and thereby establish a fluid path between said flexible chamber and said removable closure so that said liquid in said flexible chamber can be introduced to and mixed with said dry medication below said removable closure to produce a liquid medication to be absorbed by said absorbent means; and means by which to detach said removable closure from said body to expose said absorbent means therewithin so that said absorbent means can be moved into contact with the tissue area in need of treatment to apply the liquid medication thereto.

8. The applicator recited in claim 7, wherein said dry medication is a dehydrated liquid disinfectant that is rehydrated when said liquid is introduced thereto to produce said liquid medication.

9. The applicator recited in claim 7, further comprising a liquid impermeable backing located at the bottom of said applicator body, said dry medication located between said absorbent means and said liquid impermeable backing to improve the efficiency by which said absorbent means absorbs said liquid medication.

10. The applicator recited in claim 9, further comprising a base bonded to the bottom of said body so that said dry medication is sandwiched between said absorbent means and said liquid impermeable backing with said absorbent means being urged upwardly through said access opening in said body so that said absorbent means is accessible at the top of said body.

11. The applicator recited in claim 7, wherein said means by which to detach said removable closure from said body includes a pull tab extending outwardly from said removable closure to a manually accessible position at the top of said body.

12. The applicator recited in claim 11, wherein said means for detaching said removable closure from said applicator body also includes a flexible joint by which said removable closure is hingedly connected to said body, said removable closure being severed from said body at said joint when said pull tab is pulled away from said body.

13. The applicator recited in claim 12, wherein said removable closure is covered with adhesive so that said removable closure is rotatable at said flexible joint towards and adhesively bonded to the top of said applicator body to surround said access opening and said absorbent means projecting upwardly through said access opening from the bottom of said body.

14. The applicator recited in claim 7, wherein said absorbent means is a pad and said dry medication is a crystalline solid having a wafer shape.

15. An applicator for applying a liquid medication to a tissue area in need of treatment, said applicator comprising:

a body;

a flexible first chamber closed against said body;

a liquid stored within said first chamber;

a second chamber closed against said body;

a dry medication stored within said second chamber;

absorbent means located in said second chamber and communicating with said dry medication;

a fluid orifice extending between said first and second chambers, said fluid orifice being sealed against said body to close said fluid orifice and thereby block the introduction of the liquid in said first chamber to the dry medication in said second chamber, said flexible first chamber being responsive to a compressive force applied thereto to generate a corresponding hydraulic pressure within said liquid to unseal said fluid orifice from said body to open said fluid orifice and thereby establish a fluid path between said first and second chambers so that said liquid in said first chamber can be introduced to and mixed with said dry medication in said second chamber to produce a liquid medication to be absorbed by said absorbent means;

a liquid impermeable backing located within said second chamber and having an adhesive surface, said dry medication positioned between said absorbent means and the adhesive surface of said liquid impermeable backing, whereby said liquid impermeable backing is adhesively bonded to said absorbent means with said dry medication sandwiched therebetween; and means by which to open said second chamber to expose said absorbent means therewithin so that said absorbent means can be moved into contact with the tissue area in need of treatment to apply the liquid medication thereto.

16. The applicator recited in claim 15, wherein said means by which to open said second chamber includes a lateral tear line extending across said body and through said second chamber, said body being severed along said lateral tear line to rupture said second chamber and expose said absorbent means therewithin.

* * * * *